US00PP37486P2

(12) United States Plant Patent
van Dijk

(10) Patent No.: US PP37,486 P2
(45) Date of Patent: Jun. 23, 2026

(54) ***ANTHURIUM* PLANT NAMED 'AN2700430'**

(50) Latin Name: *Anthurium andreanum*
Varietal Denomination: AN2700430

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/315,589

(22) Filed: Aug. 31, 2025

(51) Int. Cl.
*A01H 5/02* (2018.01)
*A01H 6/00* (2018.01)
*A01H 6/10* (2018.01)

(52) U.S. Cl.
USPC ..... Plt./368
CPC ..... *A01H 6/00* (2018.05); *A01H 5/02* (2013.01)

(58) Field of Classification Search
USPC ..... Plt./368
See application file for complete search history.

*Primary Examiner* — Susan Mccormick Ewoldt
(74) *Attorney, Agent, or Firm* — C. Anne Whealy

(57) ABSTRACT

A new and distinct cultivar of Anthurium plant named 'AN2700430', characterized by its upright to outwardly arching plant habit; freely clumping growth habit; bushy and dense plants; narrowly deltoid dark green-colored leaves; freely flowering habit; open inflorescences that are positioned above the foliar plane on strong scapes; ovate spathes that are purplish pink in color; and dark purplish red-colored spadices.

2 Drawing Sheets

Figure 1:
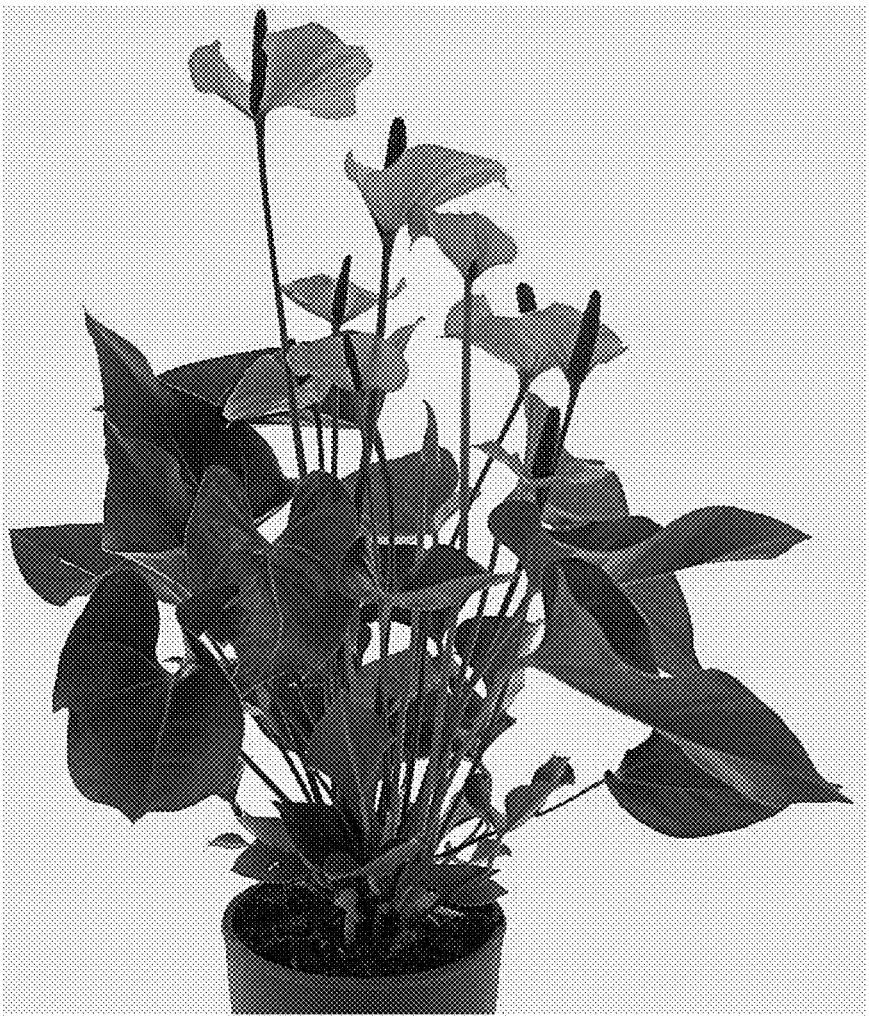

Botanical designation: *Anthurium andreanum.*
Cultivar denomination: 'AN2700430'.

CROSS-REFERENCED TO CLOSELY-RELATED APPLICATION

A European Community Plant Breeder's Rights application for the instant plant was filed by the Applicant/Assignee of the instant application, Anthura B.V. of Bleiswijk, The Netherlands on Nov. 20, 2024, application No. 2024/2691. Foreign priority is not claimed to this application.

BACKGROUND OF THE INVENTION

The present invention relates to a new and distinct cultivar of *Anthurium* plant, botanically known as *Anthurium andreanum*, commonly referred to as Flamingo Flower and hereinafter referred to by the name 'AN2700430'.

The new *Anthurium* plant is a product of a controlled breeding program conducted by the Inventor in Bleiswijk, The Netherlands. The objective of the breeding program is to create new *Anthurium* plants with durable purplish pink-colored spathes.

The new *Anthurium* plant originated from a cross-pollination made by the Inventor in April 2014 in Bleiswijk, The Netherlands of a proprietary breeding selection of *Anthurium andreanum* identified as code No. 12-028032-0007, not patented, as the female, or seed, parent with a proprietary breeding selection of *Anthurium andreanum* identified as code No. 10-025414-0004, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in May 2016.

Asexual reproduction of the new *Anthurium* plant by in vitro meristem propagation in a controlled environment in Bleiswijk, The Netherlands since March 2018 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2700430'. These characteristics in combination distinguish 'AN2700430' as a new and distinct *Anthurium* plant:

1. Upright to outwardly arching plant habit.
2. Freely clumping growth habit; bushy and dense plants.
3. Narrowly deltoid dark green-colored leaves.
4. Freely flowering habit.
5. Open inflorescences that are positioned above the foliar plane on strong scapes.
6. Ovate spathes that are purplish pink in color.
7. Dark purplish red-colored spadices.

Plants of the new *Anthurium* differ primarily from plants of the female parent selection in the following characteristics:

1. Leaf apices of plants of the new *Anthurium* are apiculate with a mucronate tip whereas leaf apices of plants of the female parent selection are narrowly acuminate.
2. Spathes of plants of the new *Anthurium* are larger than spathes of plants of the female parent selection.

Plants of the new *Anthurium* differ primarily from plants of the male parent selection in the following characteristics:

1. Plants of the new *Anthurium* have smaller spathes than plants of the male parent selection.

2. Spathes of plants of the new *Anthurium* are concave whereas spathes of plants of the male parent selection are convex.
3. Spadices of plants of the new *Anthurium* are shorter than spadices of plants of the male parent selection.

Plants of the new Anthurium can also be compared to plants of *Anthurium andreanum* 'AN2891370', disclosed in U.S. Plant Pat. No. 35,546. In side-by-side comparisons, plants of the new *Anthurium* differ primarily from plants of 'AN2891370' in the following characteristics:

1. Spathes of plants of the new *Anthurium* are purplish pink in color whereas spathes of plants of 'AN2891370' are purplish red in color.
2. Spathe apices of plants of the new *Anthurium* are mucronulate whereas spathe apices of plants of 'AN2891370' are narrowly acuminate.
3. Plants of the new *Anthurium* have shorter spadices than plants of 'AN2891370'.

BRIEF DESCRIPTION OF THE PHOTOGRAPHS

The accompanying photographs illustrate the overall appearance of the new *Anthurium*.

The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2700430' grown in a container.

Figure 2:
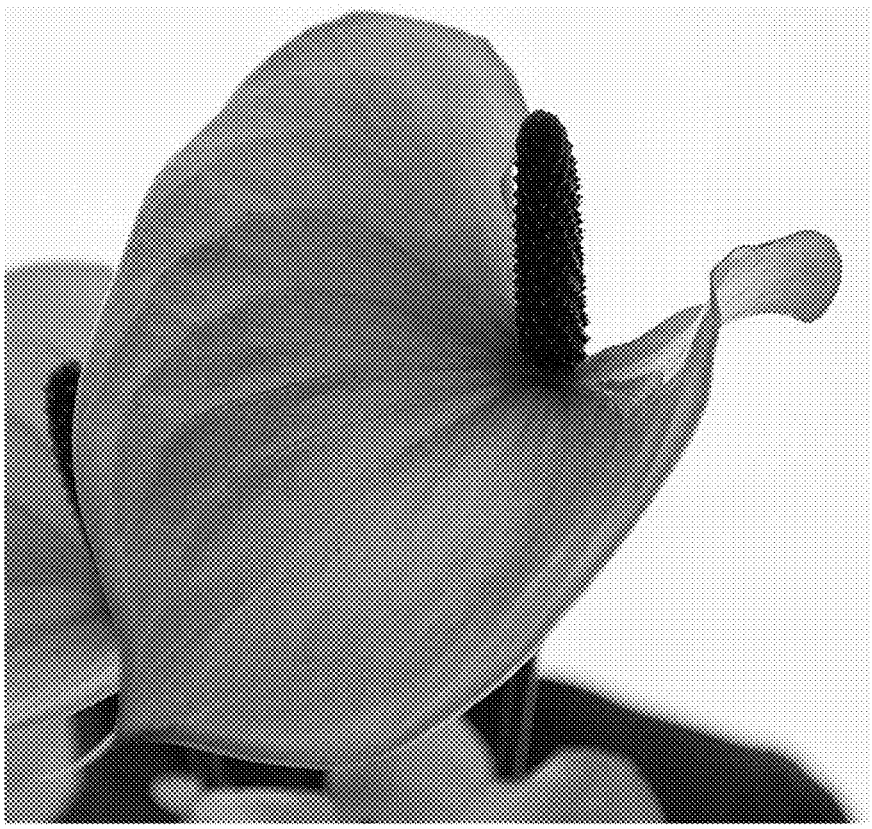

The photograph on the second sheet (FIG. 2) is a close-up view of a typical inflorescence of 'AN2700430'.

DETAILED BOTANICAL DESCRIPTION

The aforementioned photographs and following observations and measurements describe plants grown in 14-cm containers during the winter in a glass-covered greenhouse in Bleiswijk, The Netherlands. Plants were grown under conditions and practices which approximate those generally used in commercial *Anthurium* production. During the production of the plants, day and night temperatures ranged from about 19°° C. to about 22.5° C. and light levels ranged from about 100 μmol to about 200 μmol. Plants were eleven months from planting young rooted plants when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2700430'.

Parentage:

*Female, or seed, parent.*—Proprietary breeding selection of *Anthurium andreanum* identified as code No. 12-028032-0007, not patented.

*Male, or pollen, parent.*—Proprietary breeding selection of *Anthurium andreanum* identified as code No. 10-025414-0004, not patented.

Propagation:

*Type.*—By in vitro meristem propagation.

*Time to initiate roots, summer and winter.*—About two weeks at temperatures ranging from about 19° C. to about 22.5° C.

*Time to produce a rooted young plant, summer and winter.*—About six to eight weeks at temperatures ranging from about 19° C. to about 22.5° C.

*Root description.*—Medium in thickness, fibrous; typically creamy white in color; actual color of the roots is dependent on substrate composition, water quality, fertilizer type and formulation, substrate temperature and physiological age of roots.

*Rooting habit.*—Freely branching, medium density.

Plant description:

*Plant shape.*—Upright to outwardly spreading plant habit; overall shape, elliptic to ovate.

*Growth habit.*—Freely clumping habit imparting a bushy and dense appearance; in a single year of production, about 40 individual plants can be harvested per plant; moderately vigorous growth habit and moderate growth rate.

*Plant height, from soil level to top of leaf plane.*—About 30.2 cm. Plant height, from soil level to top of inflorescences: About 42.9 cm.

*Plant diameter or spread.*—About 42.8 cm.

Leaf description:

*Arrangement.*—Alternate; simple.

*Length.*—About 16.7 cm.

*Width.*—About 9 cm.

*Shape.*—Narrowly deltoid.

*Apex.*—Apiculate with a mucronulate tip.

*Base.*—Cordate.

*Margin.*—Entire; coarsely undulate.

*Texture, upper and lower surfaces.*—Smooth, glabrous; moderately coriaceous.

*Venation pattern.*—Pinnate.

*Color.*—Developing leaves, upper surface: Close to 143A; narrow marginal edges, close to 144A. Developing leaves, lower surface: Close to NN137A; narrow marginal edges, close to 144B. Fully expanded leaves, upper surface: Close to 147A; narrow marginal edges, close to 144A; mucronulate tip, close to N144C; venation, close to 144A. Fully expanded leaves, lower surface: Close to 146B; venation, close to 144C.

*Petioles.*—Length: About 16.9 cm. Diameter: Distally, about 3 mm and proximally, about 5 mm. Texture, upper and lower surfaces: Smooth, glabrous. Color, upper surface: Close to 144A. Color, lower surface: Close to a blend of 144A and 144B. Geniculum length: About 1.6 cm. Geniculum diameter: About 4 mm. Geniculum texture, upper and lower surfaces: Smooth, glabrous. Geniculum color, upper surface: Close to a blend of 144B and N144A. Geniculum color, lower surface: Close to 144A. Wing length: About 1.5 cm. Wing diameter: About 4 mm. Wing texture: Smooth, glabrous. Wing color: Close to 144A.

Inflorescence description:

*Inflorescence arrangement and flowering habit.*—Spathes with spadices; open inflorescences held above the foliar plane on strong scapes; flowering structures arise from leaf axils; freely and continuous flowering year-round in controlled temperature greenhouses in The Netherlands; typically about nine developing and developed inflorescences per plant at one time; inflorescence development commences about 2.5 to 3.5 months after planting rooted young plants.

*Inflorescence longevity.*—On the plant, depending on temperature, spathes maintain good substance for about two months; inflorescences persistent.

*Fragrance.*—None detected.

*Spathes.*—Length: About 8.7 cm. Width: About 8.4 cm. Shape: Ovate; concave. Apex: Mucronulate. Base: Cordate. Margin: Entire. Aspect: About 55° to 75° from the scape axis. Texture, upper and lower surfaces: Smooth, glabrous; moderately coriaceous. Color: When developing, front surface: Close to 186C; towards the margins, close to 62C; narrow marginal edges, close to 186A; mucronulate tip, close to 150B; venation, close to 186A. When developing, rear surface: Close to a blend of 186C and 186D; narrow marginal edges, close to 186A; mucronulate tip, close to 150C; venation, close to 184A. Fully developed, front surface: Close to 68D; towards the base, close to 65D; narrow marginal edges, close to 185B; mucronulate tip, close to 23C; venation, close to 59C; with subsequent development, main color becoming closer to 65D. Fully developed, rear surface: Close to 75D; towards the base, close to 69D; narrow marginal edges, close to 59C; mucronulate tip, close to 23C; venation, close to 59B; with subsequent development, main color becoming closer to a blend of 69A and 69B.

*Spadices.*—Length: About 4.8 cm. Diameter: About 9 mm. Shape: Cylindrical, slightly tapering towards the apex; apex, obtuse; base, obtuse; in cross-section, rounded. Aspect: About 5° to 20° from the scape axis. Color, immature and mature: Close to N79A. Flowers: Type: Hermaphroditic. Quantity per spadix: About 270. Height: About 1 mm. Diameter: About 2.5 mm. Shape: Roughly square. Anther color: Close to 155D. Pollen amount: Scarce. Pollen color: Close to 155D. Stigma color: Close to 155D.

*Scapes.*—Length: About 28.2 cm. Diameter: About 4 mm. Strength: Strong, sturdy. Aspect: About 20° from vertical. Color: Close to 146B; distally, tinged with close to 178A.

*Seed and fruit.*—To date, seed and fruit development has not been observed on plants of the new *Anthurium.*

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures of about 30° C. and to be hardy to USDA Hardiness Zone 10.

It is claimed:

1. A new and distinct *Anthurium* plant named 'AN2700430' as herein illustrated and described.

* * * * *